US00PP10151P

United States Patent [19]

Wandell

[11] Patent Number: Plant 10,151

[45] Date of Patent: Dec. 16, 1997

[54] *PYRUS CALLERYANA×BETULIFOLIA* TREE NAMED 'EDGEWOOD'

[76] Inventor: Willet N. Wandell, P.O. Box 674, Oquawka, Ill. 61469

[21] Appl. No.: 695,031

[22] Filed: Aug. 9, 1996

[51] Int. Cl.[6] ..... A01H 5/00

[52] U.S. Cl. ..... Plt./36

[58] Field of Search ..... Plt./36

[56] References Cited

U.S. PATENT DOCUMENTS

| | | | |
|---|---|---|---|
| P.P. 3,815 | 12/1975 | Flemer, III | Plt./36 |
| P.P. 4,530 | 5/1980 | Handy | Plt./36 |
| P.P. 4,591 | 9/1980 | Westwood | Plt./36 |
| P.P. 7,033 | 9/1989 | Wandell | Plt./36 |

*Primary Examiner*—James R. Feyrer
*Assistant Examiner*—Kent L. Bell

[57] ABSTRACT

This is a variety of *Pyrus calleryana×betulifolia* and has been reproduced asexually from a tree found growing in a cultivated area in Du Page County, Ill. with a growth habit of 20' wide and 25' tall without benefit of cultural pruning and trimming. When propagated by me asexually it produced straight-growing progeny with a strong central leader; a tree crown producing annually an abundance of substantially deep green leaves and flowers followed by small persistent fruit. The bark is gray-brown with reddish underbark with elongated scales broken by shallow longitudinal fissures.

3 Drawing Sheets

BACKGROUND OF THE INVENTION

This specimen of *Pyrus calleryana×betulifolia* was found growing in a cultivated area in DuPage County, Ill. in timber type soil on a rolling terrain area. The specimen was growing away from other trees and receiving the advantage of solar energy from all quarters. It had an upright growth habit and a fully developed crown with an outstanding limb structure. I have asexually produced 85 progeny from this tree by chip budding in my Oquawka, Ill. nursery. All exhibited the same acceptable characteristics of the parent tree, including the production of bloom and fruit in their fourth year which then occur annually.

SUMMARY OF INVENTION

A new and distinct cultivar of *Pyrus calleryana× betulifolia* characterized by a limited growth habit, both upright and spreading, abundance of white bloom in spring which mature to pea-sized fruit; lustrous leaves with flattened 3–7 cm. petioles which "dance" in the breeze and are disease resistant. Also, small tidy growth with well maintained symmetrical crown that does not break or spread beyond limits; once established requires little pruning or trimming.

DESCRIPTION OF THE NEW PLANT

Figure 1:
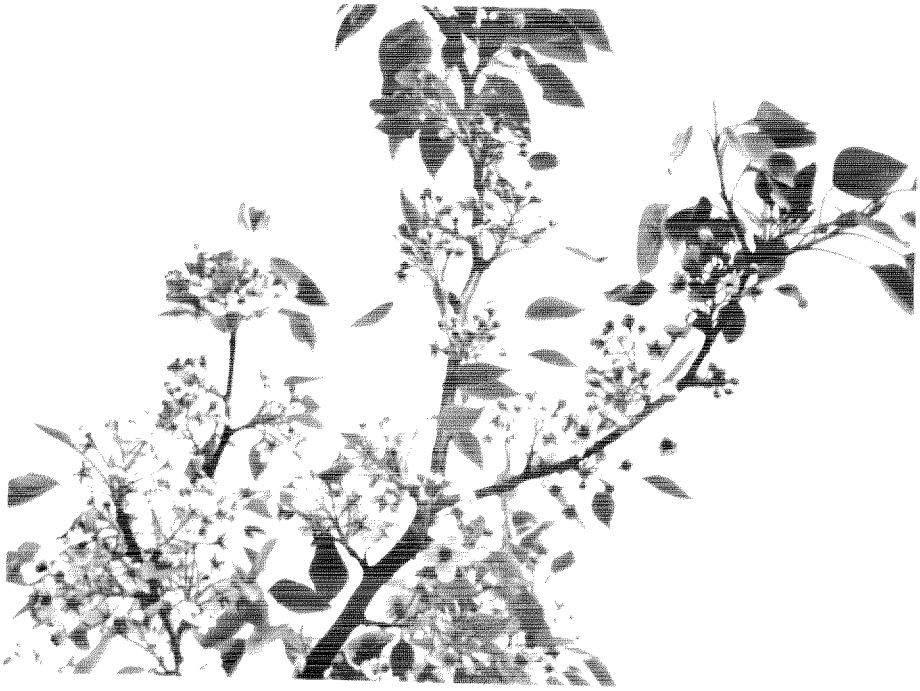
FIG. 1: Shows a branch of 'Edgewood' *Pyrus calleryana× betulifolia* in bloom exhibiting the productions of small fruit.
Figure 2:
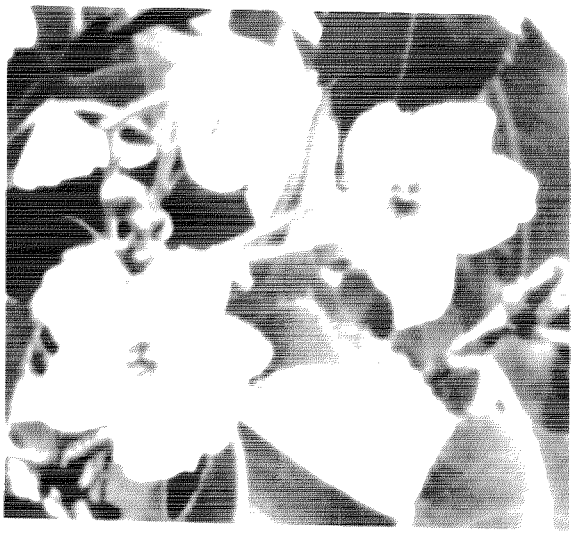
FIG. 2: Shows a close-up of the bloom including fine petals and a perfect flower.
Figure 3:
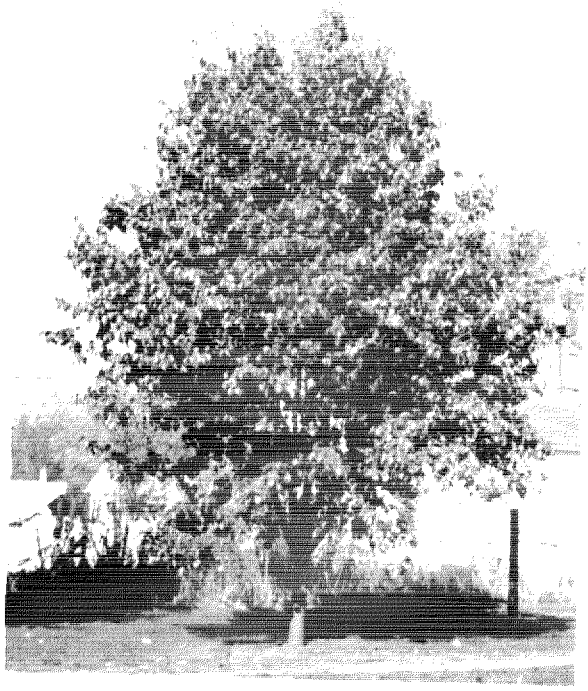
FIG. 3: Shows the tree in full summer foliage and exhibits the symmetry and adequacy of the crown including pigment in the upper reaches.
Figure 4:
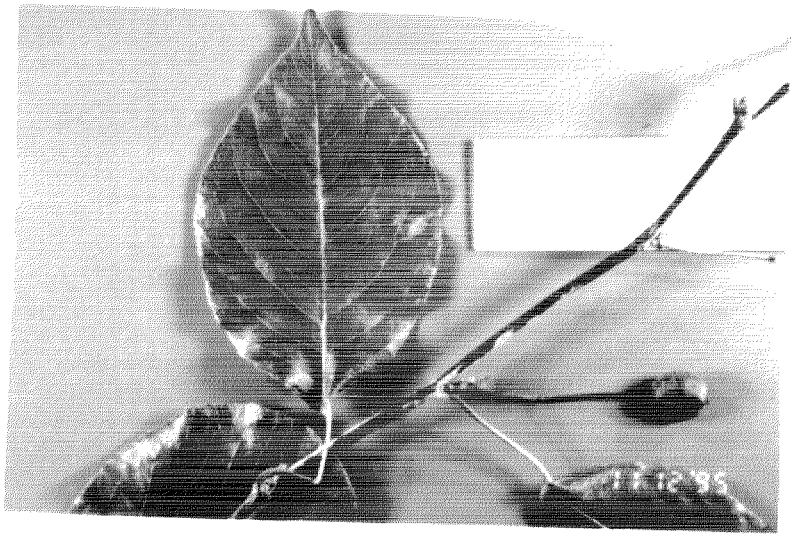
FIG. 4: Shows a close-up of the leaf and fruit of Edgewood showing the glossy nature of the leaf and small size of the fruit as it reaches full development.
Figure 5:
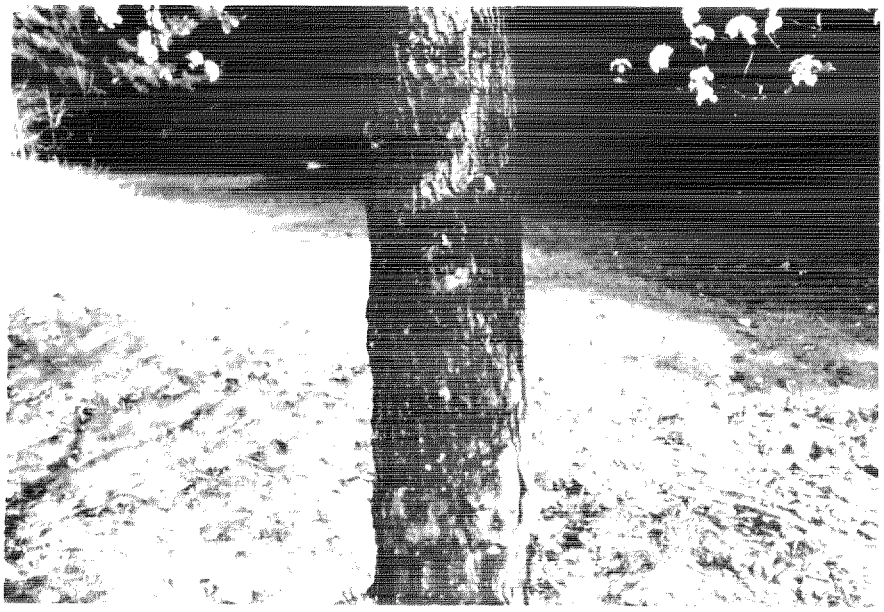
FIG. 5: Shows the furrowed, attractive nature of the bark including the elongated fissures.

The following is a detailed description of my new variety of *Pyrus calleryana×betulifolia* tree with color designations according to The R.H.S. Colour Chart published by The Royal Horticultural Society of London, England and the stated observations having been made on trees growing in Oquawka, Ill. by the applicant and found to distinguish from the species. The colors of the plant parts of this tree have been observed to not differ from those of the species in general, and are not seen to distinguish the tree. Accordingly, only verbal, general color designations are presented below.

Origin: This tree was discovered in an open planting of collected trees in DuPage County, Ill.

Parentage: a tree of unknown origin and parentage found growing in DuPage County, Ill.

Propagation: Maintains its distinguishing characteristics when propagated by Discov-Tree Research, Oquawka, Ill.

Classification: *Pyrus calleryana×betulifolia.*

Parentage: *Pyrus calleryana* and *P.×betulifolia* by assumption.

Form: A rounded, upright tree maturing 20' wide and 25' tall.

Habit: A small-sized tree with a one trunk and a single straight leader; main branches spreading; crown symmetrical, dense, closely defined, broadly pyramidal in shape. The angle of the major scaffold branching from the trunk is 45°.

Twigs: Both the long shoots from terminal buds and short lateral spurs rather stout; first year twigs of long shoots 2–5 mm in diameter, reddish brown with small elliptic lenticels, at first finely tomentose with whitish trichomes, the pubescence soon becoming patchy and the twigs finally mostly glabrous; spurs 3–4 mm in diameter with crowded remnants of leaf bases at the base, the individual leaf scars slightly raised, shallowly semi-circular with 3 bundle traces.

Winter buds: Terminal buds and lateral buds nearly the same size, both narrowly ovoid, 7–8 mm long, tomentose with whitish to yellowish trichomes; exposed bud scales about 8, the lower scales reddish brown, the upper scales paler, the scales with a prominent mid-vein and mucronate apices.

Bark: Gray-brown with reddish-brown underbark, the flat-topped elongate scales broken by shallow longitudinal fissures and is smooth in texture.

Leaves: Alternately arranged, deciduous, simple; blades elliptic, broadly elliptic, or slightly ovate, 6–10 cm long and 4–6 cm broad, the apices somewhat acuminate, the margins serrulate with somewhat upward curving teeth, the bases broadly cuneate; mature leaves glabrous above and below, the upper surfaces bright green and lustrous, the lower surfaces paler, duller; the veins camptodromous, finely reticulate; petioles elongate, 3–7 cm long, slender, flattened, 1 mm across, tomentose when emerging, becoming glabrescent; stipules very small caducous. Upper surface matches Royal Horticulture Society Colour Chart green group 141B; leaves surface matches 143A. Fall leaf coloration is reddish purple.

Inflorescences: Racemose corymbs with 8–12 flowers, the pedicels tomentose, to 3 cm long.

Flowers: Perfect, white, 2 cm across, petals 5, nearly circular, 8 mm long, the tips obtuse, the margins entire, the bases with a very short claw; calyx lobes triangular, 2.5 mm long, the tips tapering, the margins entire; stamens ca. 20, the anthers pinkish purple; styles 2, free, about equaling the stamens; ovary inferior, 2-loculate, each locule with 2 ovules.

Fruit: Pomes, small, ovoid, 1 cm long, brilliant red turning to olive-brown, the surface marked with many small circular lenticels, the calyx deciduous, the flesh containing abundant stone cells.

I claim:

1. A new and distinctive variety of *Pyrus calleryana*× *betulifolia* tree named 'Edgewood' as shown and described herein that differs from all other varieties by the unique combination of: (1) lustrous leaves with long flattened petioles that allow leaves to flutter with the wind when other vegetation is quiet; (2) good resistance to fire blight (*Erwinia amylovora*); (3) transplants easily with little shock; (4) limited growth to form a well maintained, symmetrical crown; and (5) compact growth habit that requires little pruning once established; (6) reliable flower production on the entire tree, producing small pea-sized fruit; withstands flooding for a reasonable period of time.

* * * * *